United States Patent
Lai

(10) Patent No.: US 10,766,900 B2
(45) Date of Patent: Sep. 8, 2020

(54) BARICITINIB INTERMEDIATE, METHOD FOR FORMING BARICITINIB INTERMEDIATE, AND METHOD FOR PREPARING BARICITINIB OR PHARMACEUTICALLY ACCEPTABLE SALT THEREOF

(71) Applicant: Formosa Laboratories, Inc., Taoyuan (TW)

(72) Inventor: Hsiang-Yun Lai, Taoyuan (TW)

(73) Assignee: FORMOSA LABORATORIES, INC., Taoyuan (TW)

( * ) Notice: Subject to any disclaimer, the term of this patent is extended or adjusted under 35 U.S.C. 154(b) by 53 days.

(21) Appl. No.: 15/857,755

(22) Filed: Dec. 29, 2017

(65) Prior Publication Data

US 2019/0202834 A1    Jul. 4, 2019

(51) Int. Cl.
*C07D 487/04*    (2006.01)

(52) U.S. Cl.
CPC ................ *C07D 487/04* (2013.01)

(58) Field of Classification Search
CPC .................................................. C07D 487/04
See application file for complete search history.

(56) References Cited

U.S. PATENT DOCUMENTS

| 8,158,616 | B2 | 4/2012 | Rodgers et al. | |
|---|---|---|---|---|
| 8,202,999 | B2* | 6/2012 | Sun | C07D 207/335 544/159 |
| 9,540,367 | B2 | 1/2017 | Tung | |
| 2008/0051384 | A1* | 2/2008 | Schmitz | C07D 495/04 514/210.18 |
| 2016/0257687 | A1 | 9/2016 | Zhou | |

FOREIGN PATENT DOCUMENTS

| CN | 105294699 A | 2/2016 |
|---|---|---|
| CN | 105541891 A | 5/2016 |
| CN | 106496195 A | 3/2017 |
| CN | 106496233 A | 3/2017 |
| CN | 106554363 A | 4/2017 |
| WO | WO 2016088094 A1 | 9/2016 |
| WO | WO 2016125080 A2 | 11/2016 |
| WO | WO 2016205487 A1 | 12/2016 |
| WO | WO 2017082759 A1 | 5/2017 |
| WO | WO 2017082760 A1 | 5/2017 |
| WO | WO 2017129116 A1 | 8/2017 |

OTHER PUBLICATIONS

Lin et al. (Organic Letters, 2009, 11(9), pp. 1999-2002).*
Jacks et al. (Organic Process Research & Development, 2004, 8(2), pp. 201-212).*
Saygili et al. (Org. Biomol. Chem., 2004, 2, pp. 852-857).*
Sambasivarao Kotha et al, Recent Applications of the Suzuki-Miyaura Cross-Coupling Reaction in Organic Synthesis, Elsevier Science Ltd., Sep. 8, 2002, pp. 9633-9695, Department of Chemistry, Indian Institute of Technology—Bombay, Powai, Mumbai 400 076, India, Tetrahedron 58.

* cited by examiner

*Primary Examiner* — Susanna Moore

(74) *Attorney, Agent, or Firm* — Fay Sharpe LLP

(57) ABSTRACT

The present disclosure provides a Baricitinib intermediate, a method for preparing the Baricitinib intermediate, and a method for preparing Baricitinib or a pharmaceutically acceptable salt thereof using the Baricitinib intermediate. The method for preparing the Baricitinib intermediate involves the use of a divalent palladium catalyst or a nickel catalyst and provides the Baricitinib intermediate in high yield.

12 Claims, No Drawings

BARICITINIB INTERMEDIATE, METHOD FOR FORMING BARICITINIB INTERMEDIATE, AND METHOD FOR PREPARING BARICITINIB OR PHARMACEUTICALLY ACCEPTABLE SALT THEREOF

BACKGROUND

Field of Invention

The present disclosure relates to a Baricitinib intermediate, a method for preparing the Baricitinib intermediate, and a method for preparing Baricitinib or a pharmaceutically acceptable salt thereof using the Baricitinib intermediate.

Description of Related Art

Baricitinib may play the role as a Janus kinase (JAK) inhibitor in the treatment of Rheumatoid Arthritis. In the present preparation method of Baricitinib, metal catalysts are utilized to promote the forming of a Baricitinib intermediate.

However, there are some drawbacks using the metal catalysts in the forming of the Baricitinib intermediate. Some metal catalysts are known to be oxygen sensitive. Oxidation of the metal catalysts may lead to reaction stalling or reduced reaction rate, and therefore the reaction should be handled under oxygen-free nitrogen or argon. Thus, there is a need to seek for a more convenient process for the preparation of the Baricitinib intermediate.

SUMMARY

The present disclosure provides a method for forming a compound of formula (1):

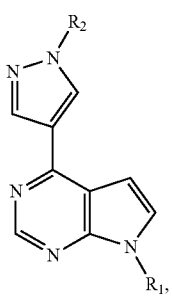

(1)

wherein $R_1$ is —$CH_2OC(O)R'$, R' is a substituted or unsubstituted alkyl group or a substituted or unsubstituted cycloalkyl group, $R_2$ is selected from the group consisting of substituted or unsubstituted cyclic ether group, 1-(ethoxy)ethyl group, p-methoxybenzyl group, triphenylmethyl group, diphenylmethyl group, hydroxymethyl group, methoxymethyl group, triisopropylsilyl group and t-butyldimethylsilylmethyl group. The method includes reacting a compound of formula (2) with a boron-containing compound selected from the group consisting of a compound of formula (3), a compound of formula (4), and a compound of formula (5) in the presence of a divalent palladium catalyst or a nickel catalyst, wherein the formula (2), the formula (3), the formula (4), and the formula (5) are as follows:

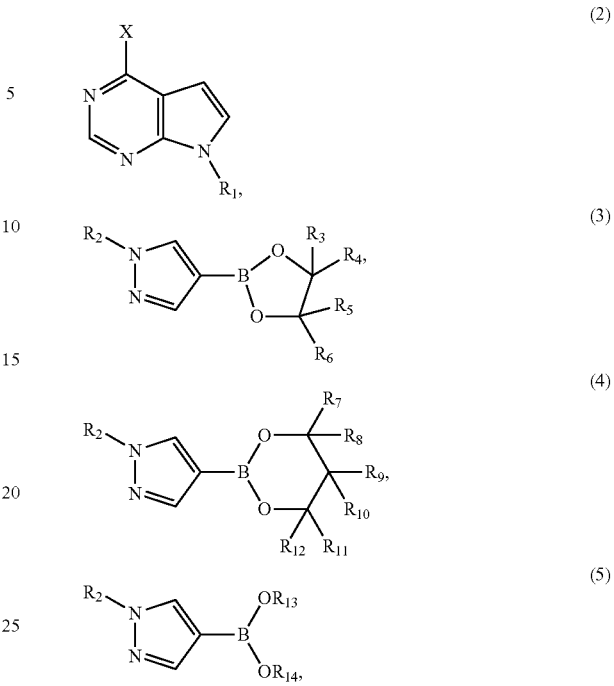

wherein X is selected from the group consisting of Br, Cl, I, tosylate group and triflate group; and $R_3$, $R_4$, $R_5$, $R_6$, $R_7$, $R_8$, $R_9$, $R_{10}$, $R_{11}$, $R_{12}$, $R_{13}$, and $R_{14}$ are each independently H or $C_1$-$C_4$ alkyl group.

In some embodiments of the method of the present disclosure, R' is a halogen-substituted alkyl group, an ether-substituted alkyl group, an aryl-substituted alkyl group, an oxytrimethylsilyl-substituted alkyl group, an alkyl-substituted cycloalkyl group, a halogen-substituted cycloalkyl group, an ether-substituted cycloalkyl group, or an aryl-substituted cycloalkyl group.

In some embodiments of the method of the present disclosure, R' is —$C_pH_{2p+1}$, and p is an integer from 1 to 15.

In some embodiments of the method of the present disclosure, $R_1$ is —$CH_2OC(O)C(CH_3)_3$.

In some embodiments of the method of the present disclosure, $R_2$ is selected from the group consisting of substituted or unsubstituted tetrahydropyranyl group, 2,3-dihydropyranyl group, and 1-(ethoxy)ethyl group.

In some embodiments of the method of the present disclosure, $R_2$ is selected from the group consisting of

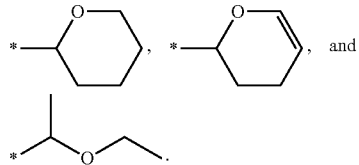

In some embodiments of the method of the present disclosure, the boron-containing compound is the compound of formula (3).

In some embodiments of the method of the present disclosure, $R_3$, $R_4$, $R_5$, and $R_5$ are methyl group.

In some embodiments of the method of the present disclosure, the divalent palladium catalyst is selected from the group consisting of bis(triphenylphosphine)palladium (II) dichloride ($Pd(PPh_3)_2Cl_2$), palladium(II) acetate ($Pd(OAc)_2$), and [1,1'-bis(diphenylphosphino)ferrocene]palladium(II) dichloride ($Pd(dppf)Cl_2$).

In some embodiments of the method of the present disclosure, the divalent palladium catalyst is $Pd(PPh_3)_2Cl_2$.

In some embodiments of the method of the present disclosure, the nickel catalyst is selected from the group consisting of bis(1,5-cyclooctadiene)nickel(0) ($Ni(COD)_2$), bis(tricyclohexylphosphine)nickel(II) dichloride ($Ni(PCy_3)_2Cl_2$), [1,1'-bis(diphenylphosphino)ferrocene]nickel(II)dichloride ($Ni(dppf)Cl_2$), bis(triphenylphosphine)nickel(II) dichloride ($Ni(PPh_3)_2Cl_2$), and $Ni(PCy_3)_2(Aryl)X$ precatalysts, wherein when X is Cl, Aryl is 1-naphthyl, 2-naphthyl, 1-acenaphthenyl, 1-(2-methoxynaphthyl), 9-phenanthrenyl, or 9-anthracyl, and when X is Br, tosylate group (OTs), or mesylate group (OMs), Aryl is 1-naphthyl or 2-naphthyl.

In some embodiments of the method of the present disclosure, the nickel catalyst is $Ni(COD)_2$.

In some embodiments of the method of the present disclosure, the method further includes reacting the compound of formula (2) with the boron-containing compound in a solvent.

In some embodiments of the method of the present disclosure, the method further includes reacting the compound of formula (2) with the boron-containing compound in the presence of a phosphine ligand.

In some embodiments of the method of the present disclosure, the reaction of the compound of formula (2) with the boron-containing compound is performed under a basic condition.

In some embodiments of the method of the present disclosure, before reacting the compound of formula (2) with the boron-containing compound, the method further includes reacting a compound of formula (6) with a compound of formula (7) to form the compound of formula (2) in the presence of potassium carbonate, wherein the formula (6) and the formula (7) are as follows:

(6)

(7)

$R_1$—Y, and Y is selected from the group consisting of Br, Cl, and I.

The potassium carbonate is advantageous to promote the forming of the compound of formula (2) in high yield and high purity, and therefore beneficial to the mass production of the compound of formula (2) and the baricitinib in succeeding steps.

The present disclosure further provides a compound of formula (8):

(8)

or a pharmaceutically acceptable salt thereof,
wherein $R_1$ is —$CH_2OC(O)R'$, R' is a substituted or unsubstituted alkyl group or a substituted or unsubstituted cycloalkyl group.

In some embodiments of the present disclosure, R' is —$C_pH_{2p+1}$, and p is an integer from 1 to 15.

In some embodiments of the present disclosure, $R_1$ is —$CH_2OC(O)C(CH_3)_3$.

The present disclosure further provides a method for preparing Baricitinib or a pharmaceutically acceptable salt thereof. The method includes: preparing the compound of formula (1) by the method described in previous embodiments, and preparing the Baricitinib or the pharmaceutically acceptable salt thereof with the compound of formula (1).

These and other features, aspects, and advantages of the present disclosure will become better understood with reference to the following description and appended claims.

It is to be understood that both the foregoing general description and the following detailed description are by examples, and are intended to provide further explanation of the disclosure as claimed.

DETAILED DESCRIPTION

Reference will now be made in detail to the present embodiments of the disclosure, examples of which are illustrated in the accompanying drawings. Wherever possible, the same reference numbers are used in the drawings and the description to refer to the same or like parts.

The disclosure provides a method for forming a compound of formula (1):

(1)

wherein $R_1$ is —$CH_2OC(O)R'$, R' is a substituted or unsubstituted alkyl group or a substituted or unsubstituted cycloalkyl group, $R_2$ is selected from the group consisting of substituted or unsubstituted cyclic ether group, 1-(ethoxy) ethyl group, p-methoxybenzyl group, triphenylmethyl group, diphenylmethyl group, hydroxymethyl group, methoxymethyl group, triisopropylsilyl group and t-butyldimethylsilylmethyl group. The method includes reacting a compound of formula (2) with a boron-containing compound selected from the group consisting of a compound of formula (3), a compound of formula (4), and a compound of formula (5) in the presence of a divalent palladium catalyst or a nickel catalyst, wherein the formula (2), the formula (3), the formula (4), and the formula (5) are as follows:

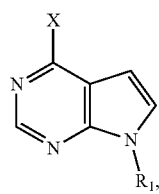
(2)

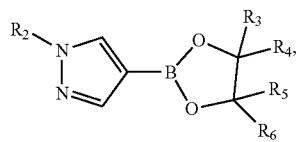
(3)

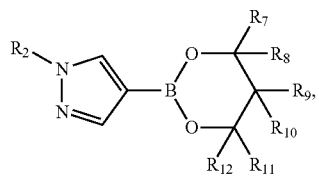
(4)

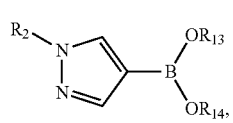
(5)

wherein X is selected from the group consisting of Br, Cl, I, tosylate group and triflate group; $R_3$, $R_4$, $R_5$, $R_6$, $R_7$, $R_8$, $R_9$, $R_{10}$, $R_{11}$, $R_{12}$, $R_{13}$, and $R_{14}$ are each independently H or $C_1$-$C_4$ alkyl group. The compound of formula (2) reacts with the boron-containing compound to form the compound of formula (1) via a Suzuki coupling reaction.

In some embodiments of the method of the present disclosure, R' is a halogen-substituted alkyl group, an ether-substituted alkyl group, an aryl-substituted alkyl group, an oxytrimethylsilyl-substituted alkyl group, an alkyl-substituted cycloalkyl group, a halogen-substituted cycloalkyl group, an ether-substituted cycloalkyl group, or an aryl-substituted cycloalkyl group.

The term "halogen" includes all four halogens, i.e., chlorine, fluorine, bromine, iodine.

The term "alkyl" includes saturated monovalent hydrocarbon radicals having straight or branched moieties. Examples of alkyl groups include, but are not limited to, methyl, ethyl, propyl, isopropyl, butyl, isobutyl, t-butyl, pentyl and hexyl.

The term "ether" includes organic compounds that contain an oxygen atom connected to two alkyl, cycloalkyl, allyl, aryl groups or the combination thereof. Examples of ether include, but are not limited to methoxy, ethoxy, aryloxy, allyloxy and their analogs and homologs.

The term "aryl" includes an organic radical derived from an aromatic hydrocarbon by removal of a hydrogen atom, such as phenyl, naphthyl, indenyl, fluorenyl, —C(CH$_3$)(C$_6$H$_5$)$_2$, and —C$_3$H$_4$(C$_6$H$_5$). "Aryl" encompasses fused ring groups wherein at least one ring is aromatic.

The term "cycloalkyl" includes non-aromatic saturated cyclic alkyl moieties wherein alkyl is as defined above. Examples of cycloalkyl groups include, but are not limited to, cyclopropyl, cyclobutyl, cyclopentyl, cyclohexyl, cycloheptyl, cyclooctyl, and the like.

In some embodiments of the method of the present disclosure, R' is a substituted or unsubstituted alkyl group having 1 to 15 carbon atoms, such as a methyl group, an ethyl group, a n-propyl group, an isopropyl group, a n-butyl group, a sec-butyl group, a t-butyl group, a n-pentyl group, a neopentyl group, a n-hexyl group, a n-heptyl group, a n-octyl group, a n-nonyl group, a n-decyl group, —C(CH$_3$)$_2$CH$_2$CH$_3$, —C(CH$_3$)$_2$(CH$_2$)$_2$CH$_3$, —C(CH$_3$)$_2$(CH$_2$)$_3$CH$_3$, —C(CH$_3$)$_2$(CH$_2$)$_{11}$CH$_3$, and —C(CH$_3$)$_2$C(CH$_3$)$_3$; a halogenated alkyl group such as a chloromethyl group, a bromomethyl group, a 1-chloroethyl group, a 2-bromo-t-butyl group, a 2-chloro-n-hexyl group, and —C(CH$_3$)$_2$CH$_2$Cl; an alkoxyalkyl group such as a methoxymethyl group, a 1-methoxyethyl group, a 2-ethoxy-t-butyl group, a 2-ethoxy-n-hexyl group, —C(CH$_3$)$_2$CH$_2$OCH$_3$, —C(CH$_3$)$_2$(CH$_2$O)$_2$CH$_3$, —C(CH$_3$)$_2$CH$_2$OC$_2$H$_4$OCH$_3$, and —C(CH$_3$)$_2$CH$_2$O(C$_2$H$_4$O)$_2$CH$_3$; an alkylthioalkyl group such as a methylthiomethyl group, a 1-methylthioethyl group, a 2-methylthio-t-butyl group, and a 4-methylthio-n-hexyl group. In some other embodiments of the present disclosure, R' is a substituted or unsubstituted cycloalkyl group having 1 to 15 carbon atoms, such as a cyclopropyl group, a cyclobutyl group, a cyclopentyl group, a cyclohexyl group, a cycloheptyl group, a cyclooctyl group, a 1-methyl-cyclopropyl group, a 1-ethyl-cyclopropyl group, a 1-methyl-cyclobutyl group, a 1-ethyl-cyclobutyl group, or a 1-methyl-cyclohexyl group; an alkoxycycloalkyl group such as a 2-methoxycyclopropyl group, a 3-ethoxycyclohexyl group, or —(CH$_3$)C$_6$H$_8$OCH$_3$; an alkylthiocycloalkyl group such as a 2-methylthiocyclopropyl group and a 3-ethylthiocyclohexyl group; a halogenated cycloalkyl group such as a 2-chlorocyclopropyl group, a 3-bromocyclohexyl group, or —(CF$_3$)C$_5$H$_8$; an aryl-substituted cycloalkyl group such as —C$_5$H$_8$(C$_6$H$_5$) In some embodiments of the method of the present disclosure, R' is —C$_p$H$_{2p+1}$, and p is an integer from 1 to 15. For example, p is 1, 2, 3, 4, 5, 6, 7, 8, 9, 10, 11, 12, 13, 14 or 15. In some embodiments, $R_1$ is —CH$_2$OC(O)C(CH$_3$)$_3$.

In some embodiments of the method of the present disclosure, $R_2$ is a substituted or unsubstituted cyclic ether group having 3 to 10 carbon atoms. In some embodiments of the method of the present disclosure, $R_2$ is selected from the group consisting of substituted or unsubstituted tetrahydropyranyl group, 2,3-hydropyranyl group, and 1-(ethoxy) ethyl group.

In some embodiments of the method of the present disclosure, $R_2$ is selected from the group consisting of

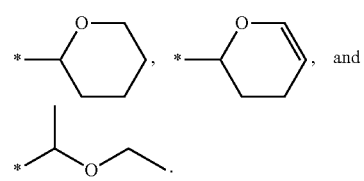

In some embodiments of the method of the present disclosure, the boron-containing compound is the compound of formula (3). In some embodiments of the method of the present disclosure, $R_3$, $R_4$, $R_5$, and $R_6$ of the compound of formula (3) are methyl group.

In some embodiments of the method of the present disclosure, the divalent palladium catalyst is selected from the group consisting of bis(triphenylphosphine)palladium (II) dichloride ($Pd(PPh_3)_2Cl_2$), palladium(II) acetate ($Pd(OAc)_2$), and [1,1'-bis(diphenylphosphino)ferrocene]palladium(II) dichloride ($Pd(dppf)Cl_2$).

Specifically, the divalent palladium catalyst is used to catalyze the Suzuki coupling reaction of the compound of formula (2) and the boron-containing compound to form the compound of formula (1). Compared with air-sensitive palladium (0) catalyst, the divalent palladium catalyst is typically air and moisture stable. Due to the stability of divalent palladium catalyst, it is advantageous to be utilized in the preparation of the compound of formula (1).

In some embodiments of the method of the present disclosure, the divalent palladium catalyst is $Pd(PPh_3)_2Cl_2$.

In some embodiments of the method of the present disclosure, the nickel catalyst is selected from the group consisting of bis(1,5-cyclooctadiene)nickel(0) ($Ni(COD)_2$), bis(tricyclohexylphosphine)nickel(II) dichloride ($Ni(PCy_3)_2Cl_2$), [1,1'-bis(diphenylphosphino)ferrocene]nickel(II)dichloride ($Ni(dppf)Cl_2$), bis(triphenylphosphine) nickel(II) dichloride ($Ni(PPh_3)_2Cl_2$), and $Ni(PCy_3)_2(Aryl)X$ precatalysts. When X is Cl, Aryl is 1-naphthyl, 2-naphthyl, 1-acenaphthenyl, 1-(2-methoxynaphthyl), 9-phenanthrenyl, or 9-anthracyl. When X is Br, tosylate group (OTs), or mesylate group (OMs), Aryl is 1-naphthyl or 2-naphthyl.

Specifically, the nickel catalyst is used to catalyze the Suzuki coupling reaction of the compound of formula (2) and the boron-containing compound to form the compound of formula (1). Compared with high-cost palladium (0) catalyst, the nickel catalyst is relatively inexpensive, and therefore it is economical to be utilized in the preparation of the compound of formula (1).

In some embodiments of the method of the present disclosure, the nickel catalyst is $Ni(COD)_2$.

In some embodiments of the method of the present disclosure, the method further includes reacting the compound of formula (2) with the boron-containing compound in a solvent. The solvent may include dioxane, toluene, tetrahydrofuran (THF), butanol, and dimethylformamide, but are not limited thereto.

In some embodiments of the method of the present disclosure, the method further includes reacting the compound of formula (2) with the boron-containing compound in the presence of a phosphine ligand. In some embodiments of the present disclosure, the phosphine ligand is tricyclohexylphosphine ($PCy_3$).

In some embodiments of the method of the present disclosure, the reaction of the compound of formula (2) with the boron-containing compound is performed under a basic condition. The basic condition may be obtained by adding one or more bases, for example, $K_2CO_3$, potassium tert-butoxide (KOtBu), $Cs_2CO_3$, $K_3PO_4$, NaOH, and trimethylamine into the reaction, but are not limited thereto.

In some embodiments of the method of the present disclosure, before reacting the compound of formula (2) with the boron-containing compound, the method further includes reacting a compound of formula (6) with a compound of formula (7) to form the compound of formula (2) in the presence of potassium carbonate, wherein the formula (6) and the formula (7) are as follows:

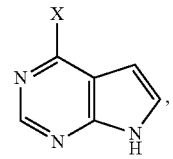

(6)

(7)

and X is selected from the group consisting of Br, Cl, I, tosylate group (OTs) and triflate group, $R_1$ is —$CH_2OC(O)R'$, R' is a substituted or unsubstituted alkyl group or a substituted or unsubstituted cycloalkyl group, and Y is selected from the group consisting of Br, Cl, and I. The reaction involves modifying the compound of formula (6) with a protecting group to form the compound of formula (2). The protecting group is contributed from the compound of formula (7), and it is denoted as $R_1$.

The present disclosure further provides a compound of formula (8):

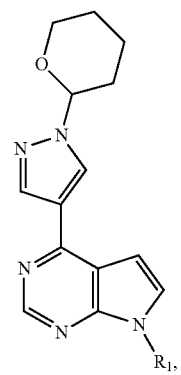

(8)

or a pharmaceutically acceptable salt thereof; wherein $R_1$ is —$CH_2OC(O)R'$, R' is a substituted or unsubstituted alkyl group or a substituted or unsubstituted cycloalkyl group. The compound of formula (8) can be formed by the method described previously. It is noted that, when $R_2$ of the formula (1) is

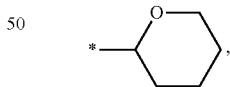

the formula (1) is the formula (8).

In some embodiments of the present disclosure, R' is —$C_pH_{2p+1}$, and p is an integer from 1 to 15. For example, p is 1, 2, 3, 4, 5, 6, 7, 8, 9, 10, 11, 12, 13, 14 or 15.

In some embodiments of the present disclosure, $R_1$ is —$CH_2OC(O)C(CH_3)_3$.

The present disclosure further provides a method for preparing Baricitinib or a pharmaceutically acceptable salt thereof. The method includes the preparing of the compound of formula (1) and the preparing of the Baricitinib or the pharmaceutically acceptable salt thereof with the compound of formula (1). Accordingly, in some embodiments, the compound of formula (1) is Baricitinib intermediate, and thus the previous method for forming the compound of formula (1) is a method for forming Baricitinib intermediate.

The disclosure of preparing of the compound of formula (1) is mentioned above, and therefore is not repeated herein. The details of the preparing of the Baricitinib or the pharmaceutically acceptable salt thereof with the compound of formula (1) are given below. The first step includes a deprotection reaction of the compound of formula (1) under an acidic condition to form a compound of formula (9):

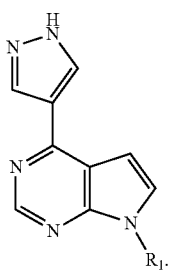

(9)

The acidic condition may be obtained by adding acid which is capable of removing $R_2$, which is used as a protecting group, such as hydrochloric acid, acetyl chloride, and/or the like, but not limited thereto.

Next, the compound of formula (9) is reacted with a compound of formula (10) to form a compound of formula (11). The compound of formula (10) and the compound of formula (11) are as follows:

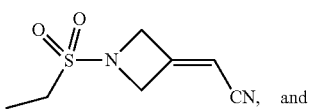

(10)

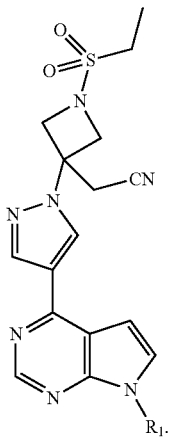

(11)

Specifically, forming of the compound of formula (11) involves a coupling reaction between the compound of formula (10) and the compound of formula (9).

Subsequently, the compound of formula (11) is reacted with an alkali, and thereby forming the baricitinib. More specifically, forming of the baricitinib involves a deprotection reaction of the compound of formula (11) in the presence of the alkali. The alkali may include lithium hydroxide, sodium hydroxide, potassium hydroxide, rubidium hydroxide, and cesium hydroxide, but not limited thereto.

The following Examples are provided to illustrate certain aspects of the present disclosure and to aid those of skill in the art in practicing this disclosure. These Examples are in no way to be considered to limit the scope of the disclosure in any manner.

Example 1

Synthesis of (4-chloro-7H-pyrrolo[2,3-d]pyrimidin-7-yl)methyl pivalate

To a solution of 4-chloro-1H-pyrrolo[2,3-b]pyridine (5.0 g, 32.56 mmol) in dimethylformamide (DMF) (20 mL), $K_2CO_3$ (5.4 g, 39.07 mmol) was added. The solution was stirred at room temperature, and chloromethyl pivalate (5.5 g, 36.52 mmol) was added dropwise into the solution at room temperature. The reaction mixture was stirred at room temperature for 16 hours. Water (50 mL) was added to the resulting solution, and the resulting suspension was stirred at room temperature for 2 hours. The solids were collected by filtration, washed with water (10 mL×2), and dried under vacuum to give (4-chloro-7H-pyrrolo[2,3-d]pyrimidin-7-yl)methyl pivalate (8.47 g) as an off-white solid.

Example 2

Synthesis of (4-(1-(tetrahydro-2H-pyran-2-yl)-1H-pyrazol-4-yl)-7H-pyrrolo[2,3-d]pyrimidin-7-yl)methyl pivalate To a suspension of (4-chloro-7H-pyrrolo[2,3-d]pyrimidin-7-yl)methyl pivalate (5 g, 18.68 mmol) in 1,4-dioxane (50 mL), 1-(tetrahydro-2H-pyran-2-yl)-1H-pyrazole-4-boronic acid pinacol ester (denoted as TAPE hereinafter) (6.23 g, 22.40 mmol) and $K_2CO_3$ (5.16 g, 37.34 mmol)/$H_2O$ (15 mL) were added at room temperature under nitrogen atmosphere. $Pd(PPh_3)_2Cl_2$ (0.262 g, 0.02 equiv) was added and the resulting mixture was heated to reflux (about 72° C.) for 3 hours. When the reaction was deemed to complete, the reaction mixture was cooled to room temperature and diluted with ethyl acetate (80 mL). The two layers were separated, and the aqueous layer was extracted with ethyl acetate (80 mL). The combined organic phase was dried over $MgSO_4$ and the residue was evaporated under vacuum to give (4-(1-(tetrahydro-2H-pyran-2-yl)-1H-pyrazol-4-yl)-7H-pyrrolo[2,3-d]pyrimidin-7-yl)methyl pivalate (10.83 g) as a red oil.

Example 3

Synthesis of (4-(1-(tetrahydro-2H-pyran-2-yl)-1H-pyrazol-4-yl)-7H-pyrrolo[2,3-d]pyrimidin-7-yl)methyl pivalate To an oven-dried tube with (4-chloro-7H-pyrrolo[2,3-d]pyrimidin-7-yl)methyl pivalate (2 g, 7.47 mmol), 1-(tetrahydro-2H-pyran-2-yl)-1H-pyrazole-4-boronic acid pinacol ester (TAPE) (2.49 g, 8.95 mmol) and $K_2CO_3$ (3.1 g, 22.43 mmol) were added. The tube was taken into a glovebox, $Ni(COD)_2$ (0.126 g, 0.458 mmol) and tricyclohexylphosphine (denoted as $PCy_3$ hereinafter) (0.25 g, 0.89 mmol) was added. Degassed t-BuOH (15 mL) and degassed water (15 mL) were added. The tube was capped and taken out of the glovebox. The mixture was heated at 40° C. for 3 hours to conduct reaction. When the reaction was deemed to complete, the reaction mixture was cooled to room temperature and diluted with ethyl acetate (40 mL). The two layers were separated, and the aqueous layer was extracted with ethyl acetate (40 mL). The combined organic phase was dried over MgSO$_4$ and the residue was evaporated under vacuum to give (4-(1-(tetrahydro-2H-pyran-2-yl)-1H-pyrazol-4-yl)-7H-pyrrolo[2,3-d]pyrimidin-7-yl)methyl pivalate (4.51 g) as an orange oil.

Example 4

Synthesis of (4-(1-(1-ethoxyethyl)-1H-pyrazol-4-yl)-7H-pyrrolo[2,3-d]pyrimidin-7-yl)methyl pivalate To an oven-dried tube with (4-chloro-7H-pyrrolo[2,3-d]pyrimidin-7-yl)methyl pivalate (2 g, 7.47 mmol), 1-(1-ethoxyethyl)-4-(4,4,5,5-tetramethyl-1,3,2-dioxaborolan-2-yl)-1H-pyrazole (denoted as ETDH hereinafter) (2.49 g, 8.95 mmol) and K$_2$CO$_3$ (3.1 g, 22.43 mmol) were added. The tube was taken into a glovebox, Ni(COD)$_2$ (0.126 g, 0.458 mmol) and PCy$_3$ (0.25 g, 0.89 mmol) was added. Degassed t-BuOH (15 mL) and degassed water (15 mL) were added. The tube was capped and taken out of the glovebox. The mixture was heated at 40° C. for 3 hours to conduct reaction. When the reaction was deemed to complete, the reaction mixture was cooled to room temperature and diluted with ethyl acetate (40 mL). The two layers were separated, and the aqueous layer was extracted with ethyl acetate (40 mL). The combined organic phase was dried over MgSO$_4$ and the residue was evaporated under vacuum to give a crude product containing a title compound (4.51 g) as an orange oil. $^1$H NMR(CDCl$_3$-d,400 MHz): δ 8.82(s, 1H), 8.39(s, 1H), 8.23(s, 1H), 7.41(d, 1H, J=4 Hz), 6.72(d, 1H, J=3.6 Hz), 6.20(s, 2H), 5.45~5.42(m, 1H), 4.06~4.03(m, 1H), 3.73~3.66(m,1H), 2.22~1.60(m, 6H), 1.11(s, 9H) ppm. LCMS calculated for C$_{20}$H$_{25}$N$_5$O$_3$ (M+H)$^+$: 383.1957. Found: 384.4.

Example 5

Synthesis of (4-(1H-pyrazol-4-yl)-7H-pyrrolo[2,3-d]pyrimidin-7-yl)methyl pivalate To a solution of the crude product containing (4-(1-(tetrahydro-2H-pyran-2-yl)-1H-pyrazol-4-yl)-7H-pyrrolo[2,3-d]pyrimidin-7-yl)methyl pivalate (10.83 g, 7.16 g theoretical, 18.67 mmol) in methanol (MeOH) (72 mL) at 5° C.-10° C., acetyl chloride (4.4 g, 56.05 mmol) was added dropwise. The mixture was warmed to room temperature to conduct reaction for 6 hours. When the reaction was deemed to complete, the reaction mixture was cooled to 5° C.-10° C. The reaction mixture was quenched with 1M NaOH aqueous solution (60 mL); further adding enough basic solution to adjust the pH of the mixture solution to 9-10. The mixture was concentrated under reduced pressure to remove most of the MeOH and the resulting suspension was stirred at room temperature for 90 min. The solids were collected by filtration, washed with water (20 mL×2), and dried under vacuum to give (4-(1H-pyrazol-4-yl)-7H-pyrrolo[2,3-d]pyrimidin-7-yl)methyl pivalate (5.28 g) as an off-white solid.

Example 6

Synthesis of (4-(1H-pyrazol-4-yl)-7H-pyrrolo[2,3-d]pyrimidin-7-yl)methyl pivalate To a solution of the crude product containing (4-(1-(1-ethoxyethyl)-1H-pyrazol-4-yl)-7H-pyrrolo[2,3-d]pyrimidin-7-yl)methyl pivalate (1.2 g, 1.86 mmol) in THF (6.9 mL) at 5° C.-10° C., 4M HCl aqueous solution (1.4 mL, 5.6 mmol) was added dropwise. The mixture was warmed to room temperature to conduct reaction for 6 hours. When the reaction was deemed to complete, the reaction mixture was cooled to 5° C.-10° C. The reaction mixture was quenched with 1M NaOH aqueous solution (6 mL); further adding enough amount of the basic solution to adjust the pH of the mixture solution to 9-10. The mixture was concentrated under reduced pressure to remove most of the THF and the resulting suspension was stirred at room temperature for 30 min. The solids were collected by filtration, washed with water (5 mL×2), and dried under vacuum to give (4-(1H-pyrazol-4-yl)-7H-pyrrolo[2,3-d]pyrimidin-7-yl)methyl pivalate (0.42 g) as an off-white solid. $^1$H NMR (DMSO-d$_6$, 400 MHz): δ 13.40 (br s, 1H), 8.76 (s, 1H), 8.66 (s, 1H), 8.33 (s, 1H), 7.69 (d, 1H, J=4 Hz), 7.11 (d, 1H, J=3.6 Hz), 6.23 (s, 2H), 1.08 (s, 9H) ppm. $^{13}$C NMR (DMSO-d$_6$, 100 MHz): δ 176.99, 151.56, 151.38, 151.19, 138.76, 129.61, 119.77, 113.22, 101.17, 66.51, 38.23, 26.52 ppm. LCMS calculated for C$_{15}$H$_{17}$N$_5$O$_2$ (M+H)$^+$: 300.1416. Found: 300. LCMS calculated for C$_{15}$H$_{16}$N$_5$O$_2$Na (M+Na)$^+$: 322.1235. Found: 322.

Example 7

Synthesis of 4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate A suspension of (4-(1H-pyrazol-4-yl)-7H-pyrrolo[2,3-d]pyrimidin-7-yl)methyl pivalate (1.5 g, 5.01 mmol) and 2-(1-(ethylsulfonyl)azetidin-3-ylidene)acetonitrile (EAYA) (0.95 g, 5.10 mmol) in DMF (4.5 mL) was cooled to 5° C.-10° C., then 1,8-diazabicyclo(5.4.0)undec-7-ene (DBU) (0.045 g, 0.06 mmol) was added dropwise into the solution to keep the temperature between 5° C.-10° C. After adding DBU, the mixture was stirred at 5° C.-10° C. to conduct reaction for 3 hours. When the reaction was deemed to complete, the reaction mixture was quenched with acetonitrile (12 mL) and water (18 mL). The resulting suspension was stirred at room temperature for 1 hour. The solids were collected by filtration, washed with a mixture of acetonitrile and water (⅔ by volume, 3 mL×2), and dried under vacuum to give 4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate (2.248 g) as an off-white solid.

Example 8

Synthesis of Baricitinib

A suspension of 4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate (1.0 g, 2.06 mmol) and lithium hydroxide (0.15 g, 6.26 mmol) in acetonitrile (8 mL) and isopropanol (2 mL) was heated at 45° C.-50° C. to conduct reaction for 17 hours. When the reaction was deemed to complete, the reaction mixture was cooled to 5° C.-10° C. and 0.5M HCl aqueous solution (6 mL) as added to adjust the pH of the solution to 7-8. After adding of the acid, the mixture was stirred at 10±5° C. for 1 hour. The solids were collected by filtration, washed with water (5 mL×2), and dried under vacuum to give Baricitinib (0.383 g) as an off-white solid.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for forming a compound of formula (1):

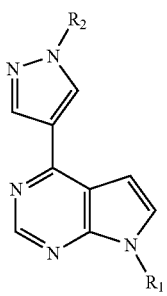

(1)

wherein $R_1$ is $CH_2OC(O)R'$, R' is a substituted or unsubstituted alkyl group or a substituted or unsubstituted cycloalkyl group, and $R_2$ is selected from the group consisting of substituted or unsubstituted cyclic ether group, 1-(ethoxy)ethyl group, p-methoxybenzyl group, triphenylmethyl group, diphenylmethyl group, hydroxymethyl group, methoxymethyl group, triisopropylsilyl group and t-butyldimethylsilylmethyl group, comprising:

reacting a compound of formula (2) with a boron-containing compound selected from the group consisting of a compound of formula (3), a compound of formula (4) and a compound of formula (5) in the presence of bis(triphenylphosphine)palladium(II) dichloride ($Pd(PPh_3)_2Cl_2$) and in the absence of an additional phosphine ligand, wherein the formula (2), the formula (3), the formula (4), and the formula (5) are as follows:

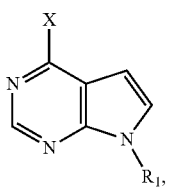

(2)

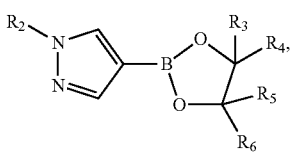

(3)

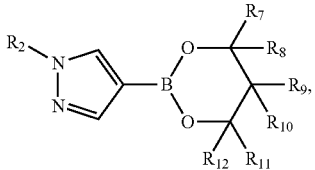

(4)

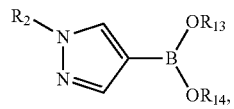

(5)

wherein X is selected from the group consisting of Br, Cl, and I; and $R_3$, $R_4$, $R_5$, $R_6$, $R_7$, $R_8$, $R_9$, $R_{10}$, $R_{11}$, $R_{12}$, $R_{13}$ and $R_{14}$ are each independently H or $C_1$-$C_4$ alkyl group.

2. The method of claim 1, wherein R' is a halogen-substituted alkyl group, an ether-substituted alkyl group, an aryl-substituted alkyl group, an oxytrimethylsilyl-substituted alkyl group, an alkyl-substituted cycloalkyl group, a halogen-substituted cycloalkyl group, an ether-substituted cycloalkyl group or an aryl-substituted cycloalkyl group.

3. The method of claim 1, wherein R' is $-C_pH_{2p+1}$, and p is an integer from 1 to 15.

4. The method of claim 1, wherein $R_1$ is $-CH_2OC(O)C(CH_3)_3$.

5. The method of claim 1, wherein $R_2$ is selected from the group consisting of substituted or unsubstituted tetrahydropyranyl group, 2,3-dihydropyranyl group, and 1-(ethoxy)ethyl group.

6. The method of claim 1, wherein $R_2$ is selected from the group consisting of

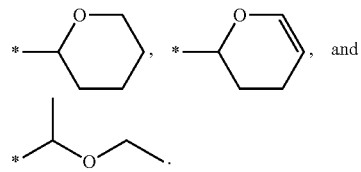

7. The method of claim 1, wherein the boron-containing compound is the compound of formula (3).

8. The method of claim 7, wherein $R_3$, $R_4$, $R_5$, and $R_6$ are methyl group.

9. The method of claim 1, further comprising reacting the compound of formula (2) with the boron-containing compound in a solvent.

10. The method of claim 1, wherein reacting the compound of formula (2) and with boron-containing compound is performed under a basic condition.

11. The method of claim 1, before reacting the compound of formula (2) with the boron-containing compound, further comprising:

reacting a compound of formula (6) with a compound of formula (7) to form the compound of formula (2) in the presence of potassium carbonate, wherein the formula (6) and the formula (7) are as follows:

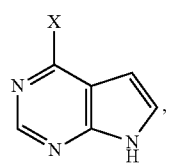

(6)

$R_1$—Y, (7)

and Y is selected from the group consisting of Br, Cl, and I.

12. A method for preparing Baricitinib or a pharmaceutically acceptable salt thereof, comprising:
- forming a compound of formula (1) according to the method of claim 1; and
- using the compound of formula (1) as an intermediate to form the Baricitinib or the pharmaceutically acceptable salt thereof.

* * * * *